United States Patent
Tarassenko et al.

(10) Patent No.: US 6,839,659 B2
(45) Date of Patent: Jan. 4, 2005

(54) SYSTEM AND METHOD FOR ACQUIRING DATA

(75) Inventors: Lionel Tarassenko, Oxford (GB); Neil William Townsend, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 10/311,245

(22) PCT Filed: Jun. 8, 2001

(86) PCT No.: PCT/GB01/02549

§ 371 (c)(1), (2), (4) Date: Apr. 10, 2003

(87) PCT Pub. No.: WO01/97092

PCT Pub. Date: Dec. 20, 2001

(65) Prior Publication Data

US 2003/0171898 A1 Sep. 11, 2003

(30) Foreign Application Priority Data

Jun. 16, 2000 (GB) .............................. 0014854

(51) Int. Cl.⁷ .............................. G06F 1/12; H04L 7/00
(52) U.S. Cl. ......................... 702/187; 375/355; 713/400
(58) Field of Search ................................ 375/355, 360, 375/365, 369, 354, 356, 362, 364, 359; 702/187, 79; 370/503; 713/400, 500, 600, 501, 502, 503

(56) References Cited

U.S. PATENT DOCUMENTS

| | | | |
|---|---|---|---|
| 4,882,739 A | * 11/1989 | Potash et al. ................ | 375/109 |
| 5,027,297 A | 6/1991 | Garitty et al. | |
| 5,140,519 A | 8/1992 | Friesdorf et al. | |
| 5,471,631 A | * 11/1995 | Beardsley et al. .......... | 713/502 |
| 5,578,063 A | 11/1996 | Bocek et al. | |
| 5,682,328 A | 10/1997 | Roeber et al. | |
| 5,704,366 A | * 1/1998 | Tacklind et al. ............ | 128/716 |
| 5,802,545 A | * 9/1998 | Coverdill ...................... | 711/35 |
| 5,921,938 A | 7/1999 | Aoyama et al. | |
| 6,279,058 B1 | * 8/2001 | Gulick ......................... | 713/400 |

FOREIGN PATENT DOCUMENTS

| | | |
|---|---|---|
| EP | 0283106 A | 9/1988 |
| GB | 2054861 A | 2/1981 |
| WO | 96/10233 A1 | 4/1996 |
| WO | 00/16223 A1 | 3/2000 |

* cited by examiner

Primary Examiner—Marc S. Hoff
Assistant Examiner—Paul L Kim
(74) Attorney, Agent, or Firm—Nixon & Vanderhye, P.C.

(57) ABSTRACT

A system for acquiring, and displaying, data such as physiological data, from a plurality of data connection devices, each of which monitor one or more different parameters and output data at different sampling frequencies based on their own system clocks. The system receives the data signals at different sampling frequencies and associates each sample of each signal with a time stamp derived from a single master clock. Low rate and high rate data are treated differently. Low rate data is associated with the current value of the master clock, where as high rate data is time stamped by giving the first sample a time stamp equal to the current value of the current master clock, subsequent samples being given an estimated time stamp based on the expected interval between samples derived from the sampling frequency of the data collection device, and the timescale given to the first example. The estimated time stamp may be periodically corrected, and the estimation calculation can be improved by correcting the value used for the interval between samples. The different signals can be displayed together on a display aligned with respect to a time axis. The system can display, the data in two different timescales, one showing a few seconds of data and one showing a few hours of data. The data traces are scrolled across the time axis, new data being added to one end of the trace.

45 Claims, 3 Drawing Sheets

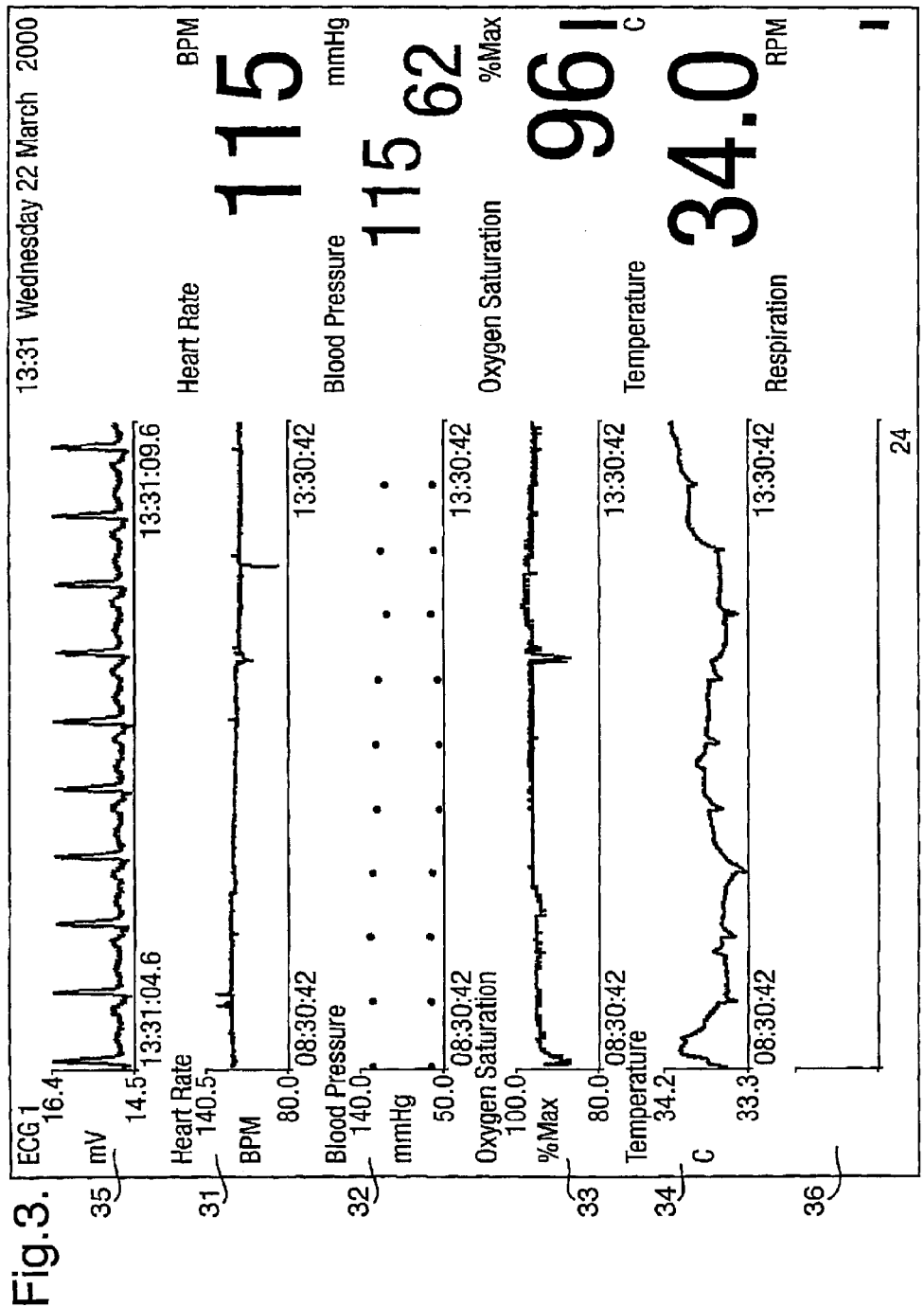

SYSTEM AND METHOD FOR ACQUIRING DATA

This application is the US national phase of international application PCT/GB01/02549 filed Jun. 8, 2001, with designated the US.

TECHNICAL FIELD

This invention relates to the acquisition of data from a plurality of data collection devices each monitoring one or more different parameters, and in particular to the synchronisation of that data.

BACKGROUND AND SUMMARY

There are many different situations in which a system is monitored by a plurality of sensors. Often such sensors are part of different data collection devices, and monitor the same or different parameters of the system. In this situation each of the data collection devices may include its own clock controlling the sampling of the data signal it is monitoring. These clocks may be free running with respect to each other. Thus the output signals from the devices may not be synchronised and may be at widely differing rates.

For instance, it is normal when monitoring the condition of a patient to monitor a variety of physiological parameters such as the electrocardiogram (which can be multiple channel), blood pressure, respiration, oxygen saturation using pulse oximetry and temperature. Typically these are acquired by different data collection devices and all are acquired at different sampling rates. For example electrocardiograms (ECG) are typically collected at 256 Hz, pulse oximetry waveforms are typically acquired at 81.3 Hz, respiration waveforms at 64 Hz, temperature at 1 Hz and blood pressure once every 10 or 20 minutes. All of these vital signs are of clinical significance and are usually displayed so that medical staff can easily monitor the condition of the patient. However, because all are measured at different rates, and typically by different pieces of apparatus with respective system clocks within them, displaying the different parameters together in a concise and synchronised way is difficult.

In order to overcome the problem of synchronizing the different signals, one solution has been proposed which is to drive all of the different monitors by the same clock signal. However, this requires that all of the monitors are, in essence, integrated which is expensive and inflexible, and further this makes existing equipment redundant.

The display of the data is also rendered difficult because parameters such as the ECG trace vary on a fast timescale compared to parameters such as blood pressure (which is only measured every 10 to 20 minutes). Thus the timing of samples in an ECG trace needs to be accurately recorded. However, the timing of samples of the blood pressure can be of lower accuracy without the loss of clinical significance.

Similar problems arise in other systems, such as plant monitoring and control, e.g. of chemical processing plants, monitoring and control of machines, such as engines or vehicle systems.

According to the present invention there is provided a system for acquiring data from a plurality of data collection devices each monitoring a parameter and outputting a data signal at a respective sampling frequency based on respective system clocks, the system comprising data processing means having:
input means for receiving data signals from each of the plurality of data collection devices;
a master clock for providing a master clock signal; and
time stamping means for associating a time stamp derived from the master clock with each of the data signals.

Thus the invention allows data to be collected from a variety of different data collection devices, but the data samples are given a timestamp which is synchronised with a master clock.

The timestamp may have a higher resolution than the master clock. The master clock produces a new time value at regular intervals. The number of such intervals within a second is known as the tick-rate. The resolution on the time axis is the inverse of the tick-rate.

Preferably the time stamp associated with the samples is calculated in a different way depending on the sampling frequency of the data signal. For data signals (such as in a physiological environment the blood pressure or temperature) whose sampling frequency is below a predetermined threshold, each sample of the data is associated with a time stamp which is simply the value of the master clock signal at the time the data is given the timestamp. However for data signals whose sampling frequency is above the predetermined threshold (such as in a physiological environment the ECG, pulse oximetry or respiration waveforms) a first sample (or an appropriate sample in a first batch) of the data signal is associated with the value of the master clock signal at the time of time stamping, but subsequent samples are provided with an estimated time stamp. This may be based on a time interval calculated from the sampling frequency of the data collection device providing that signal (based on the known specifications of the data collecting device).

Preferably the estimate is periodically compared with the current value of the master clock to determine whether the difference between them is acceptable, or greater than a predetermined amount. If it is greater than the predetermined amount then the time stamp is corrected. Further, the time stamps of a contiguous set of samples preceding the current sample are also adjusted, for instance by adjusting them so that they are evenly spaced in time up to the current sample. The predetermined difference below which correction is regarded as unnecessary may be a multiple (between 5 and 50, for example) of the master clock's resolution and the predetermined threshold of sampling frequency may be less than or equal to the master clock frequency, preferably less than one fifth of the master clock frequency.

As well as adjusting the time stamps of the set of samples preceding the current sample, the manner in which the time stamp is estimated for future samples can be adjusted by adjusting the value of sampling interval used in the calculation. Thus by correcting that value it is hoped that the estimated time stamp will not diverge (or not diverge so quickly) from the value of the master clock. This adjustment can be achieved using a Kalman filter in which the value for the accuracy of the sampling interval is set in accordance with the time taken for the estimated time stamp to diverge significantly from the master clock.

In one embodiment for use in monitoring a physiological system (such as a patient) the system is suitable for receiving and displaying signals from an ECG monitor, oxygen saturation monitor, respiration monitor, blood pressure monitor and thermometer, or indeed any other transducer or monitor used for acquiring physiological data.

Preferably the system is based around a data processing device, which incorporates the master clock, the time stamping means and the display, and the system may be ruggedized so as to be easily portable without risk of damage.

To improve the clarity of the display the data may be displayed selectively on one of two different timescales which may be referred to as a short term continuous timescale, e.g. a "beat-to-beat" timescale in a physiological environment, as in which the time axis shows a short period of data in detail, e.g. a few seconds of data (typically from 1 to 60), and a "trend" timescale in which the time axis shows a longer section of data, e.g. a few hours of data (typically this may go from 1 minute to 1 day).

The parameters displayed and the manner of their display may be varied between the two types of display. For instance, on displaying data at the first timescale, data sampled at a low sampling frequency, can be displayed as a numerical value, rather than a continuous trace (which would have little meaning at this timescale given its much lower sampling frequency). On the other hand, in the "trend" timescale it may be useful still to display a single high frequency trace at the shorter timescale so that a continuous visual check of this trace can be maintained, even though the rest of the data is viewed over a long timescale. Preferably key values for the system, such as in the physiological environment the heart rate, blood pressure, oxygen saturation and temperature, are always displayed as numerical values alongside the traces in both display modes.

As a further improvement of the display the representations of the signals, namely the traces, may be scrolled with respect to the time axis as the data signals are received. This contrasts with the normal practice when displaying signals of refreshing the displayed trace repeatedly.

The invention provides a corresponding method of synchronizing data signals and the invention maybe embodied as a computer program comprising program code means for carrying out the method. The invention thus extends to a computer-readable storage medium carrying such a program.

BRIEF DESCRIPTION OF THE DRAWINGS

The invention will be further described by way of non-limitative example with reference to the accompanying drawings in which:

FIG. 3 shows an example of the "trend" display mode of the embodiment of FIG. 1.

DESCRIPTION OF EXAMPLE EMBODIMENTS

An embodiment of the invention will be described applied to the monitoring of physiological parameters, though the invention can be applied to any system being monitored by devices running on independent clocks. Typical examples include vehicles, manufacturing or processing plants, control or monitoring systems for instance for the environment.

Figure 1:
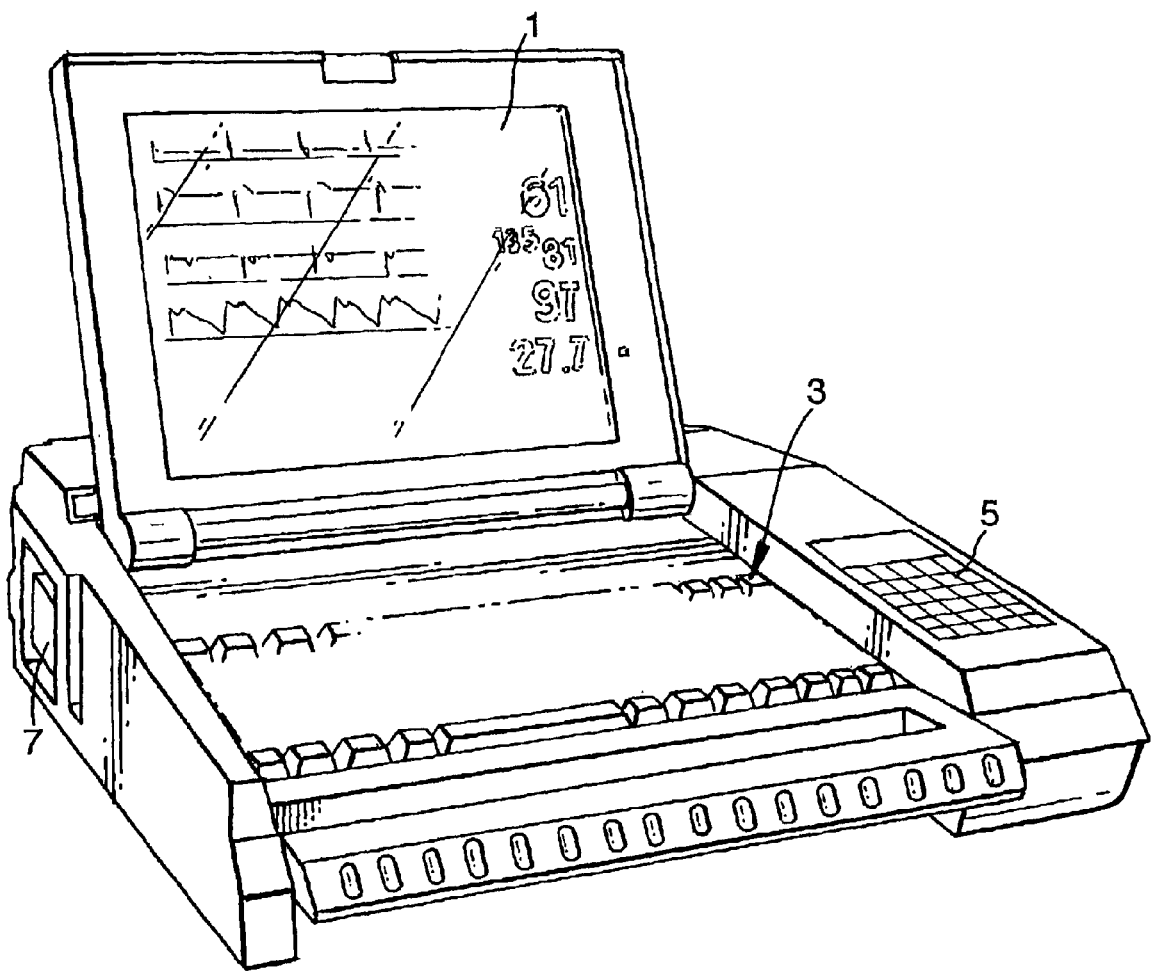
FIG. 1 shows an acquisition and display apparatus according to an embodiment of the invention.

Referring to FIG. 1 the illustrated embodiment of the invention is based on a ruggedized laptop computer which includes a display (1) a keyboard (3) and touchpad (5) as data input devices and connectors (7) to which can be connected the various types of data collection device from which physiological data is to be acquired.

This embodiment of the invention is suitable for receiving signals from such devices as an electrocardiograph, blood pressure monitor, respiration monitor, oxygen saturation monitor and thermometer and, as will be appreciated from the discussion above, typically all of these signals are acquired by those devices at different sampling rates. This embodiment of the invention provides for the display, and storage, of these parameters synchronised with each other. Thus although each of the data collection devices has an independent clock which is free-running relative to the clocks of the other devices, the invention provides for the time stamping of each sample of data from each data collection device with respect to a master clock. In this embodiment this is the master clock of the laptop computer, which has a resolution of approximately $\frac{1}{18}$th of a second.

The master clock used in this embodiment is sufficiently accurate, but has a rather low resolution, particularly compared to the timescale of the ECG trace. Further, this embodiment is designed to allow for the processing of the data in batches. In order to achieve this the incoming data from the devices is separated into two classes. The first class is low-rate data, which arrives at a frequency of less than $\frac{1}{10}$th of the resolution of the master clock, and may actually arrive at irregular intervals. The second class is high-rate data which arrives at a higher frequency. The higher frequency data is generally generated at a regular rate.

In this embodiment the data arriving at low rate, such as blood pressure measurements or temperature, are time stamped with a sample from the master clock. In other words, each sample of data is associated with the value of the master clock at the time of time stamping of the data.

The high rate data is treated differently. The first sample received (or an appropriate sample in a first batch) is given a time stamp from the master clock. An expected time interval between samples from the data collection device providing this physiological data is estimated based on the specifications of the data collection device. Thus, quite simply, for an ECG where the sampling rate is 256 Hz, the estimated interval is $\frac{1}{256}$ seconds. Subsequent samples of the data following the first are then given an estimated time stamp which is the time stamp for the previous sample plus the expected time interval.

In order to allow for the estimated time stamp diverging from the master clock, at regular intervals (e.g. a low multiple of the resolution of the master clock typically 5 to 50), the time stamp given to a sample is compared with the current value of the master clock. In batch processing this is done on the last value in the batch to give maximum accuracy through the batch. If the time stamp given to the sample and the master clock are in close agreement, i.e within a low multiple of the master clock's resolution, then the process continues. However, if the agreement is insufficient, two procedures are carried out:

a) The time stamp of that sample is corrected to the current value from the master clock and a sufficiently long contiguous set of previous (e.g. covering one second or so) samples have their time stamp adjusted so that they are evenly spaced up to the new time stamp given to the current sample.

b) Also the value of the time interval used in the estimate of the time stamps is corrected. Thus rather than using the value calculated from the specifications of the data collection device, that value is adjusted to try to achieve lower divergence from the master clock. The correction can be weighted according to the accuracy of the clock and the accuracy of the estimated time interval, for instance using a Kalman filter cycle in which the accuracy of the expected time interval is related to the length of time it takes for a timing error to be deemed to have occurred. However, the adjustment can be made in different ways.

Thus the incoming data from the data collection devices is synchronized in software and this avoids the need to drive the different data collection devices using a single master clock.

Figure 2:
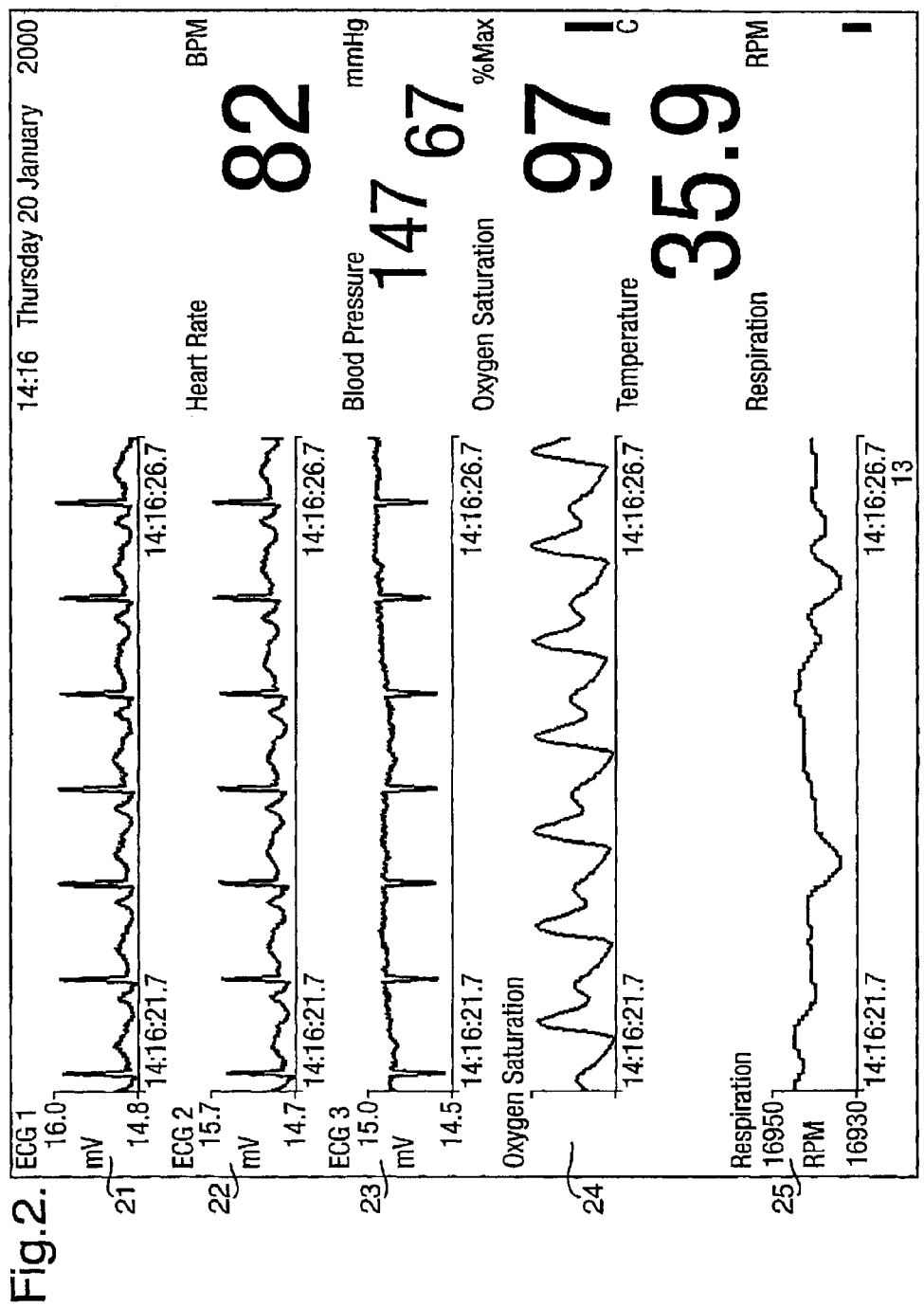
FIG. 2 illustrates an example of a "beat-to-beat" display mode of the embodiment of FIG. 1.

The synchronized data is, in this embodiment, stored on a hard disk or a 1-gigabyte PCMCIA disk allowing 96 hours of continuous synchronized patient data or it can be transmitted to a remote store. Further, the synchronization of the data allows the signals from the different data collection devices to be displayed on the single display 1 aligned with respect to the time axis. Examples of the displays are shown in FIGS. 2 and 3. In this embodiment the data may be displayed in two different modes, a "beat-to-beat" mode in which five seconds of data are displayed graphically (see FIG. 2), and a "trend" mode in which five hours of data is displayed (see FIG. 3). The user can switch selectively between the two modes, and because all of the data received is time stamped and stored the user can zoom in on key events by switching from the trend mode to the corresponding time point in the beat-to-beat mode. Further, in this embodiment the displays are scrolled along the time axis with new data being added on the right hand side. This contrasts with a typical display of clinical data in which one trace is generated and displayed, e.g from left to right, and then that trace is refreshed, again, from left to right, by new data being overwritten on the old trace.

Referring in more detail to FIG. 2, which shows the beat-to-beat mode, it can be seen that three channels of ECG are displayed as traces 21, 22 and 23 together with an oxygen saturation trace 24 and a respiration trace 25. The five traces are aligned vertically one above the other on a time axis showing five seconds of data. In addition important vital signs are shown in numerical fashion on the right hand side of the display, these being the heart rate, blood pressure, oxygen saturation and temperature.

This beat-to-beat mode display can be compared with the longer timescale trend display in FIG. 3. In FIG. 3 the traces 31, 32, 33 and 34 show data for a five hour period. This timescale can be varied as desired so that data covering from one minute to one day can be displayed. Trace 31 shows the heat rate in beats per minute, trace 32 shows the blood pressure in millimeters of mercury (and it can be seen that values of the systolic and diastolic blood pressure are displayed one above the other, but they only appear every 20 minutes or so), the trace 33 shows the oxygen saturation and trace 34 shows the temperature. It should also be noted that although the display is in the "trend" mode, nevertheless a single channel of ECG trace 35 is shown at the faster timescale (i.e. 5 seconds of data over the time axis). This allows proper monitoring of the current condition of the patient. The respiration can also be displayed as a trace at 36.

In a similar fashion to the beat-to-beat mode display, numerical values of the key parameters are shown on the right hand side of the display.

It should be appreciated that the system can be adapted to acquire different physiological parameters from different types of data collection device, using the same time stamping principles.

What is claimed is:

1. A system for acquiring data from a plurality of data collection devices each monitoring one or more parameters and outputting a data signal at a respective sampling frequency based on respective system clocks, the system comprising
    data processing means including:
        input means for receiving the data signals from each of the plurality of data collection devices;
        a master clock for providing a master clock signal; and
        time stamping means for associating a time stamp derived from the master clock with each of the data signals, wherein
            for data signals whose sampling frequency is below a predetermined threshold, the time stamping means associates as the time stamp a sample of the master clock signal, and
            for data signals whose sampling frequency is above the predetermined threshold, the time stamping means associates as an initial time stamp for a sample of the data signal a sample of the master clock signal and, for subsequent samples of the data signal, estimated time stamps.

2. A system according to claim 1, farther comprising:
    a display for displaying a representation of the data signals aligned with respect to a time axis on the basis of said respective time stamps.

3. A system according to claim 1, wherein the time stamp has a higher resolution than the master clock.

4. A system according to claim 1, wherein the estimated time stamps are based on a time interval calculated from the sampling frequency of the data collection device providing the data signal and the initial time stamp.

5. A system according to claim 1, wherein the predetermined threshold is n/m of the master clock frequency, where m is a positive integer and n is a non-zero positive integer less than m.

6. A method according to claim 5, wherein the predetermined threshold is 1/10 of the master clock frequency.

7. A system according to claim 1, which is operable with data collection devices whose system clocks are free-running with respect to the master clock.

8. A system according to claim 1, further comprising a data storage device for storing the data samples and time stamps.

9. A system according to claim 1, wherein the signals are physiological signals.

10. A system according to claim 1, wherein the input means comprises interfaces for receiving signals from at least two of: an ecg monitor, oxygen saturation monitor, respiration monitor, blood pressure monitor, thermometer, intra-cranial pressure monitor, partial oxygen pressure monitor and partial carbon dioxide pressure monitor.

11. A system according to claim 1, wherein the displayed representations of the data signals are scrolled with respect to the time axis as the data signals are received.

12. A system according to claim 1, wherein the data processing means comprises a comparator, and wherein, for the data signals whose sampling frequency is above the predetermined threshold, the comparator periodically compares the estimated time stamp being associated with the current sample with the master clock to determine the difference between them and, if the difference is greater than a predetermined amount, the data processing means corrects the estimated time stamp to correspond to the master clock signal.

13. A system according to claim 12, wherein, if the difference is greater than the predetermined amount, the data processing means adjusts the time stamps of a contiguous set of samples preceding the current sample.

14. A system according to claim 13, wherein the data processing means adjusts the time stamps of the contiguous set of samples preceding the current sample by an equal fraction of the difference such that they are evenly spaced in time up to the current sample.

15. A system according to claim 13, wherein the number of samples in the contiguous set is substantially the number of samples acquired in one second.

16. A system according to claim 13, wherein the estimated time stamps are based on a time interval calculated from the sampling frequency of the data collection device providing the data signal and the initial time stamp, and, if the difference is greater than predetermined amount, the data processing means produces the estimated time stamps for subsequent samples based on an adjusted value of the time interval.

17. A system according to claim 16, wherein the data processing means comprises a Kalman filter for calculating the adjusted value of the time interval.

18. A system according to claim 16, wherein the data processing means comprises calculating means for calculating the value of the accuracy of the time interval in accordance with the time taken for the predetermined amount to be reached.

19. A system according to claim 2, comprising a laptop computer incorporating the master clock, the time stamping means and the display.

20. A system according to claim 2, wherein the data processing means and the display are adapted to display a representation of the data signals selectively on one of two different timescales.

21. A system according to claim 20, wherein the two different timescales are a first timescale of a few seconds to a few minutes and a second timescale of one minute to a few days.

22. A system according to claim 21, wherein the first timescale is such that less than thirty seconds of the time axis is displayed.

23. A system according to claim 21, wherein the first timescale is such that less than ten seconds of the time axis is displayed.

24. A system according to claim 21, wherein on displaying the representation of the data at the first timescale, data sampled at a low sampling frequency is displayed as a numeric value.

25. A system according to claim 21, wherein the second timescale is such that more than one hour of the time axis is displayed.

26. A system according to claim 21, wherein the second timescale is such that five or more hours of the time axis is displayed.

27. A system according to claim 21, wherein on displaying the representation of the data at the second timescale, one trace of data sampled at a high sampling frequency is simultaneously displayed at the first timescale.

28. A system according to claim 27, wherein the one trace of data is an ecg trace.

29. A method of synchronising data signals from a plurality of data collection devices, each monitoring a parameter and outputting a data signal at a respective sampling frequency based on respective system clocks, the method comprising associating a time stamp derived from a master clock with each of the data signals,
wherein associating the time stamp comprises:
for data signals whose sampling frequency is below a predetermined threshold, associating as the time stamp a sample of the master clock signal; and
for data signals whose sampling frequency is above the predetermined threshold, associating as an initial time stamp for a sample of the data signal a sample of the master clock signal, and, for subsequent samples of the data signal, estimated time stamps.

30. A method according to claim 29, wherein the time stamp has a higher resolution than the master clock.

31. A method according to claim 29, wherein the estimated time stamps are based on a time interval calculated from the sampling frequency of the data collection device providing the data signal and the initial time stamp.

32. A method according to claim 29, wherein the predetermined threshold is less than or equal to the master clock frequency.

33. A method according to claim 32, wherein the estimated time stamps are based on a time interval calculated from the sampling frequency of the data collection device providing the data signal and the initial time stamp and, if the difference is greater than a predetermined amount, the estimated time stamp for subsequent samples is based on an adjusted value of the time interval.

34. A method according to claim 33, comprising a Kalman filtering process for calculating the adjusted value of the time interval.

35. A method according to claim 33, wherein the value of the accuracy of the time interval is calculated in accordance with the time taken for the predetermined amount to be reached.

36. A method according to claim 29, wherein, for the data signals whose sampling frequency is above the predetermined threshold, the estimated time stamp being associated with the current sample is periodically compared with the master clock signal to determine the difference between them and, if the difference is greater than a predetermined amount, the estimated time stamp is corrected to correspond to the master clock signal.

37. A method according to claim 36, wherein, if the difference is greater than the predetermined amount, the time stamps of a contiguous set of samples preceding the current sample are adjusted.

38. A method according to claim 37, wherein the time stamps of the contiguous set of samples preceding the current sample are adjusted by an equal fraction of the difference such that they are evenly spaced in time up to the current sample.

39. A method according to claim 37, wherein the number of samples in the contiguous set is substantially the number of samples acquired in one second.

40. A method according to claim 39, wherein the signals are physiological signals.

41. A method according to claim 29, wherein the signals comprise signals from at least two of: an ecg monitor, oxygen saturation monitor, respiration monitor, blood pressure monitor, thermometer, intra-cranial pressure monitor, partial oxygen pressure monitor and partial carbon dioxide pressure monitor.

42. A computer-readable medium for storing executable instructions for performing the method of claim 29.

43. A system for acquiring data from a plurality of data collection devices each monitoring one or more parameters and outputting a data signal at a respective sampling frequency based on respective system clocks, the system comprising:
inputs receiving the data signals from each of the plurality of data collection devices;
a master clock providing a master clock signal; and
a time stamping device for associating a time stamp derived from the master clock with each of the data signals, wherein
for data signals whose sampling frequency is below a predetermined threshold, the time stamping device associates as the time stamp a sample of the master clock signal, and
for data signals whose sampling frequency is above the predetermined threshold, the time stamping device associates as an initial time stamp for a sample of the data signal a sample of the master clock signal and, for subsequent samples of the data signal, estimated time stamps.

44. A system according to claim 43, wherein each estimated time stamp is determined by adding an estimated time interval derived from the sampling frequency of the data collection device providing the data signal to a previous time stamp.

45. A system according to claim 43, wherein the inputs, the master clock and the time stamping device are embodied as a computer device.

* * * * *